(12) United States Patent
Askin et al.

(10) Patent No.: US 6,239,280 B1
(45) Date of Patent: May 29, 2001

(54) PROCESS FOR SYNTHESIZING BIARYL INHIBITORS OF FARNESYL-PROTEIN TRANSFERASE

(75) Inventors: David Askin, Warren; Jennifer A. Cowen, Somerville; Peter E. Maligres, Scotch Plains; J. Christopher McWilliams, Basking Ridge; Marjorie S. Waters, Cranbury, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/345,209

(22) Filed: Jun. 30, 1999

(51) Int. Cl.$^7$ .................................................. C07D 101/00
(52) U.S. Cl. .............................................................. 546/256
(58) Field of Search ............................................. 546/256

(56) References Cited

U.S. PATENT DOCUMENTS

| | | |
|---|---|---|
| 5,300,650 | 4/1994 | Nabata . |
| 5,453,506 | 9/1995 | Diehr . |
| 6,077,849 | * 7/2000 | Liu et al. . |

OTHER PUBLICATIONS

Begley, et al., Novel β–Lactams derived from the Photoisomer of N–Benzolxycarbonyl–methylene–2–pyridone, 1981, J.C.S. Perkin I, pp. 2620–2624.

Giam, et al., A Convenient Method for the Preparation of N–Substituted 2(1H)–Pyridones, 1977, Organic Preparations and Procedures Int., 9(1), pp. 5–8.

De Villers, et al., The Action of p–Toluenesulphonyl Chloride on Pyridine–N–Oxide1), 1956, Recueil, vol. 75, pp. 1303–1308.

Kaye, et al., N–Vinylation of Heteroaromatic O–Trimethylsilyl Lactims, 1970, Tetrahedron, vol. 26, pp. 1369–1376.

Almena, et al., Selective Alkylation of 2–Pyridone in Solvent–Free Conditions, 1994, Synthetic Communications, 24(8), pp. 1057–1063.

Liu, et al., Selective N–Functionalization of 6–Substituted–2–Pyridones, 1995, Tetrahedrom Letters, vol. 36, No. 49, pp. 8917–8920.

Liu, et al., Lewis Acid Induced Rearrangement of 2,3–Epoxy Amines; Characterisation of Aziridinium Ion Intermediates and Regiospecific Ring Opening with Nitrogen Nucleophiles, 1994, J. Chem. Soc. Perkin Trans., vol. 1, pp. 1363–1365.

Gill, et al., Lewis Acid–Induced Rearrangement of 2,3–Epoxy Sulfides: Regiospecific Nucleophilic Trapping of Thiiranium Ion Intermediates with Nitrogen Nucleophiles, 1993, J. Chem. Soc. Perkin Trans. 1, pp. 1371–1372.

Comins, et al., N– vs. O–Alkylation in the Mitsunobu Reaction of 2–Pyridone, 1994, Tetrahedron Letters, vol. 35, No. 18, pp. 2819–2822.

Sato, et al., CsF in Organic Synthesis. Tunin of N– or O–Alkylation of 2–Pyridone, Aug. 1995, Synlett, pp. 845–846.

Pyman, et al., A New Synthesis of 4(or 5–) –β–Aminoethyl–glyoxaline, one of the Active Principles of Ergot, 1911, J. Chem. Soc., vol. 99, pp. 668–682.

Duncia, et al., The Discover of Potent Nonpeptide Aniotensis II Recoptor Antagonists: A New Class of Potent Antihypertensives, 1990, J. Med. Chem., vol. 33, pp. 1312–1329.

Carini, et al., Nonpeptide Angiotensis II Receptor Antagonists: N[(Benzyloxy)benzyl]imidazoles and Related Compounds as Potent Antihypertensives, 1990, J. Med. Chem., vol. 33, pp. 1330–1336.

Jones, et al., Studies on Imidazole Compounds, I. A Synthesis of Imidazoles with Functional Groups in the 2–Position, 1949, J. Am. Chem. Soc. vol, 71, pp. 383–386.

Marckwald, Ein Beitrag sur Kenntniss der Imidazole und der Constitution des Glyoxalins, Chem. Ber., 1892, 25, pp. 2354–2373.

Renger, Direkte N–Arylierung von Amiden: Eine Verbesserung der Goldberg–Reaktion, 1985, Synthesis–Stuttgart, pp. 856–860.

Jones, et al., Studies on Imidazole Compoudns. I. A Synthesis of Imidazoles with Functional Groups in the 2–Position, Feb. 1949, J. Am. Chem. Soc., vol. 71, pp. 383–386.

Duncia, et. al., "The Discovery of Potent Nonpeptide Angiotensin II Receptor Antagonists: A New Class of Potent Antihypertensives", J. Med. Chem. 33, pp. 1312–1329, 1990.*

* cited by examiner

Primary Examiner—John Kight
Assistant Examiner—Binta Robinson
(74) Attorney, Agent, or Firm—David A. Muthard; Mark R. Daniel

(57) ABSTRACT

The present invention is directed to a process for synthesizing 1,5 disubstituted imidazoles with biaryl components of the formula (I):

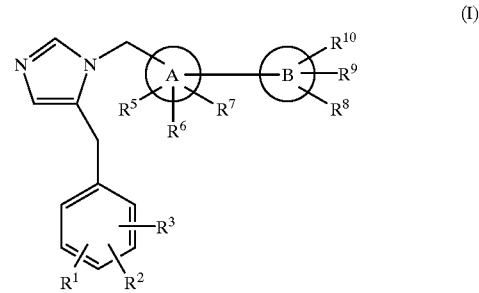

which are usefull as Farnesyl-Protein Transferase inhibitors.

16 Claims, No Drawings

PROCESS FOR SYNTHESIZING BIARYL INHIBITORS OF FARNESYL-PROTEIN TRANSFERASE

BACKGROUND OF THE INVENTION

The Ras proteins (Ha-Ras, Ki4a-Ras, Ki4b-Ras and N-Ras) are part of a signaling pathway that links cell surface growth factor receptors to nuclear signals initiating cellular proliferation. Mutated ras genes (Ha-ras, Ki4a-ras, Ki4b-ras and N-ras) are found in many human cancers, including colorectal carcinoma, exocrine pancreatic carcinoma, and myeloid leukemias.

Ras must be localized to the plasma membrane for both normal and oncogenic functions. At least three post-translational modifications are involved with Ras membrane localization, and all three modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke, Ann. Rev. Biochem. 61:355–386 (1992); W. R. Schafer and J. Rine, Ann. Rev. Genetics 30:209–237 (1992)).

The peptide derived inhibitors of farnesyl-protein transferase (FPTase) that have been described are generally cysteine containing molecules that are related to the CAAX motif that is the signal for protein prenylation. (Schaber et al., J. Biol. Chem., 265:14701–14704 (1990); Reiss et. al., Cell, 62:81–88 (1990); Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, while deletion of the thiol from a CAAX derivative has been shown to reduce the inhibitory potency of the compound, the thiol group can adversely affect the pharmacokinetics, pharmacodynamics and toxicity of FPTase inhibitors. Consequently, functional replacements for the thiol group have been achieved.

Thiol replacements that incorporate a 1,5 disubstituted imidazole with a biaryl component have been observed to be FPTase inhibitors. The synthesis of 1,5 disubstituted imidazoles from primary amines, dihydroxyacetone and potassium thiocyanate via thioimidazoles has been reported in the classical literature (Marckwald, Chem Ber. 1892, 25, 2354; Duncia, J. M. et al, J. Med Chem. 1990, 33, 1312–1330; Jones, R. G., J. Am. Chem. Soc. 1949, 71, 383 and 644; Pyman, J. Chem. Soc. 1911, 99, 668). Literature protocols for the dethionation of 2-mercaptoimidazoles describe treatment with concentrated nitric acid, with or without a nitrite; such procedures give variable results and often result in the sudden violent release of nitrogen oxide gases.

Therefore, the need exists for a process for synthesizing 1,5 disubstituted imidazoles with biaryl components which has a predictably higher yield than known methods and which utilizes reaction conditions that are free from the drawbacks described above.

SUMMARY OF THE INVENTION

The present invention provides a novel process for the preparation of compounds with the formula (I), which are useful as FPTase inhibitors:

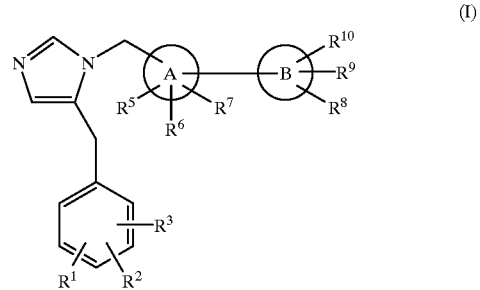

(I)

wherein:
$R^1$, $R^2$ and $R^3$ are independently selected from:
a) hydrogen,
b) aryl, substituted aryl, heterocycle, substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{11}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{11}_2N$—C(NR$^{11}$)—, CN, NO$_2$, $R^{11}C(O)$—, $N_3$, —N(R$^{11})_2$, or $R^{12}OC(O)NR^{11}$—, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{11}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{11}_2N$—C(NR$^{11}$)—, CN, $R^{11}C(O)$—, $N_3$, —N(R$^{11})_2$, or $R^{11}OC(O)NH$—;

$R^5$, $R^6$ and $R^7$ are independently selected from:
a) hydrogen,
b) unsubstituted or substituted aryl, unsubstituted or substituted heterocycle, $C_3$–$C_{10}$ cycloalkyl, halogen, $C_1$–$C_6$ perfluoroalkyl, $R^{13}O$—, $R^{12}S(O)_m$—, $R^{11}C(O)NR^{11}$—, $(R^{11})_2NC(O)$—, $R^{12}C(O)O$—, $R^{11}_2N$—C(NR$^{11}$)—, $R^{11}C(O)$—, —N(R$^{11})_2$, or $R^{12}OC(O)NR^{11}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $R^{13}O$—, $R^{12}S(O)_m$—, $R^{11}C(O)NR^{11}$—, $(R^{11})_2NC(O)$—, $R^{11}_2N$—C(NR$^{11}$)—, $R^{11}C(O)$—, —N(R$^{11})_2$, and $R^{12}OC(O)NR^{11}$—;

$R^8$, $R^9$ and $R^{10}$ are independently selected from:
a) hydrogen,
b) unsubstituted or substituted aryl, unsubstituted or substituted heterocycle, $C_3$–$C_{10}$ cycloalkyl, halogen, $C_1$–$C_6$ perfluoroalkyl, $R^{13}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{12}C(O)O$—, $R^{11}_2N$—C(NR$^{11}$)—, $R^{11}C(O)$—, —N(R$^{11})_2$, or $R^{12}OC(O)NR^{11}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $R^{13}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{11}_2N$—C(NR$^{11}$)—, $R^{11}C(O)$—, —N(R$^{11})_2$, and $R^{12}OC(O)$—NR$^{11}$—; or
any two of $R^8$, $R^9$ and $R^{10}$ on adjacent carbon atoms are combined to form a diradical selected from —CH═CH—CH═CH—, —CH═CH—CH$_2$—, —(CH$_2)_4$— and —(CH$_2)_3$—;

A is:
   a 5, 6 or 7 membered carbocyclic ring wherein from 0 to 3 carbon atoms are replaced by a heteroatom selected from N, S and O, and wherein A is attached to B through a carbon atom;

B is:
   a 4, 5, 6 or 7 membered heterocyclic ring which comprises a nitrogen atom through which B is attached to A and 0–2 additional heteroatoms selected from N, S and O, and which also comprises a carbonyl, thiocarbonyl, —C(=NR$^{14}$)— or sulfonyl moiety adjacent to the nitrogen atom attached to A;

$R^{11}$ is independently selected from hydrogen, $C_1$–$C_6$ alkyl, amino-$C_1$–$C_6$ alkyl, N-(unsubstituted or substituted benzoyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{12}$ is independently selected from $C_1$–$C_6$ alkyl and aryl;

$R^{13}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$R^{14}$ is selected from hydrogen, $C_1$–$C_6$ alkyl, $C_1$–$C_6$ alkyl-sulfonyl and $C_1$–$C_6$ acyl;

m is 0, 1 or 2.

Compounds of the formula (I) are synthesized by dethionating a thioimidazole of the formula (II):

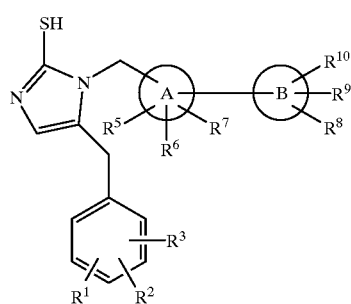

The thioimidazole of formula (II) is prepared by coupling a hydroxyketone of formula (III):

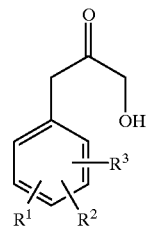

with a benzylic amine of formula (IV):

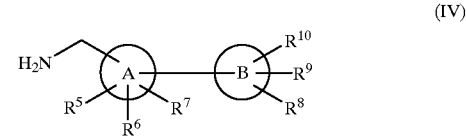

The instant invention also involves the synthesis of the novel hydroxyketone of formula (III) and the novel benzylic amine of formula (IV).

DETAILED DESCRIPTION OF THE INVENTION

The present invention is directed to a novel process for the separation of compounds of the formula (I):

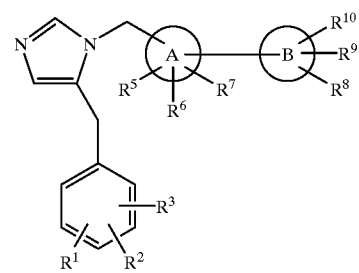

(wherein $R^1$, $R^2$, $R^3$, $R^5$, $R^6$, $R^7$, $R^8$, $R^9$, $R^{10}$, A and B are defined as set forth above)

which comprises dethionating a thioimidazole of formula (II):

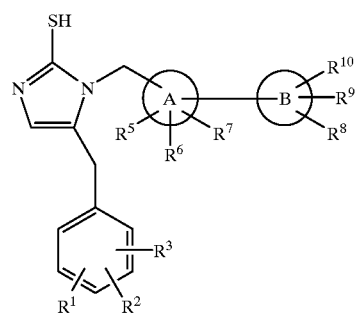

(wherein $R^1$, $R^2$, $R^3$, $R^5$, $R^6$, $R^7$, $R^8$, $R^9$, $R^{10}$, A and B are defined as set forth above)

with an oxidizing agent in the presence of a first acid. The thioimidazole of formula (II) is prepared by condensing a hydroxyketone of the formula (III):

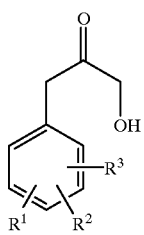

(III)

wherein R¹, R² and R³ are defined as set forth above) with a benzylic amine of the formula (IV):

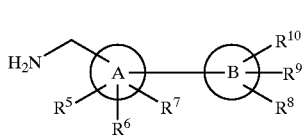

(IV)

(wherein R⁵, R⁶, R⁷, R⁸, R⁹, R¹⁰ and A and B are defined as set forth above)
in the presence of a thiocyanate and a second acid.

Oxidizing agents suitable for the dethionation of the thioimidazole of formula (II) include: hydrogen peroxide, nitric acid, nitrous acid, nitrite salts and nitrite esters. Preferred oxidizing agents for this step include: hydrogen peroxide and nitrous acid. The most preferred oxidizing agents for this step include aqueous $NaNO_2$ or aqueous $KNO_2$, which are added to an acidic solution of the thioimidazole.

First acids suitable for the dethionation of the thioimidazole of formula (II) include: anhydrous or aqueous HF, HCl, HBr, HI, sulfuric, phosphoric, MsOH, TsOH, carboxylic acids and TFA. Preferred first acids for this step include: MsOH and carboxylic acids such as HOAc and TFA. The most preferred first acid for this step is HOAc.

A suitable temperature range for the dethionation of the thioimidazole of formula (II) is about −50 to about 250° C., with a preferred temperature range being about −20 to about 100° C. and the most preferred temperature range being about −10 to about 40° C.

Dethionation of the thioimidazole of formula (II) may be run neat. However, solvents suitable for the dethionation include: water; alcohols such as MeOH, EtOH, n-PrOH, i-PrOH, butanols and alkoxyethanols; hydrocarbons such as toluene or xylenes; chlorinated hydrocarbons such as dichloromethane, chloroform, chlorobenzene and ODCB; nitriles such as acetonitrile, propionitrile, benzolitrile and tolunitrile; ketones such as acetone, MEK, MIBK and cyclohexanone; ethers such as diethyl ether, MTBE, THF, DME and DEM; other polar aprotic solvents such as formamide, DMF, DMA, NMP, DMPU, DMSO, and sulfolane; acids such as anhydrous or aqueous HF, HCl, HBr, HI, sulfuric, phosphoric, MsOH, TsOH, carboxylic acids such as HOAc and TFA. Preferred solvents for this step include: water or acids such as anhydrous or aqueous, MsOH, carboxylic acids such as HOAc and TFA. The most preferred solvents for this step include: water HOAc and TFA.

Thiocyanates suitable for the condensation of the hydroxyketone of formula (III) and the benzylic amine of formula (IV) include: LiSCN, NaSCN, KSCN, CsSCN, MgSCN, CaSCN, guanidine thiocyanate, HSCN and TMS-SCN. Preferred thiocyanates for this step include: NaSCN and KSCN. The most preferred thiocyanate for this step is KSCN.

Second acids suitable for the condensation of the hydroxyketone of formula (III) and the benzylic amine of formula (IV) include: anhydrous or aqueous HF, HCl, HBr, HI, sulfuric, phosphoric, MsOH, TsOH, ammonium halides, phosphate salts, carboxylic acids such as HOAc and TFA. Preferred second acids for this step include: anhydrous or aqueous HF, HCl, HBr, HI, ammonium halides, carboxylic acids such as HOAc and TFA. The most preferred second acid for this step is HOAc.

A suitable temperature range for the condensation of the hydroxyketone of formula (III) and the benzylic amine of formula (IV) is about −50 to about 250° C., with a preferred temperature range being about 0 to about 100° C. and the most preferred temperature range being about 50 to about 75° C.

Condensation of the hydroxyketone of formula (III) and the benzylic amine of formula (IV) may be run neat. However, solvents suitable for the condensation include: water; alcohols such as MeOH, EtOH, n-PrOH, i-PrOH, butanols and alkoxyethanols; hydrocarbons such as toluene or xylenes; chlorinated hydrocarbons such as dichloromethane, chloroform, chlorobenzene and ODCB; esters such as EtOAc, IPAC and BuOAc; nitrites such as acetonitrile, propionitrile, benzonitrile and tolunitrile; ketones such as acetone, MEK, MIBK and cyclohexanone; ethers such as diethyl ether, MTBE, THO, DME and DEM; other polar aprotic solvents such as formamide, DMF, DMA, NMP, DMPU, DMSO, and sulfolane or mixtures thereof. Preferred solvents for this step include: water; alcohols such as MeOH, EtOH, n-PrOH, i-PrOH and butanols; nitriles such as acetonitrile, propionitrile, benzonitrile and tolunitrile; mixtures of nitriles with toluene and mixtures of nitriles with water. The most preferred solvents for this step include: water, butanol, acetonitrile, a mixture of acetonitrile and water or a mixture of acetonitrile and toluene.

One embodiment of the instant invention involves the preparation of a compound of formula (IV), which is useful as an intermediate in the preparation of compounds of formula (I):

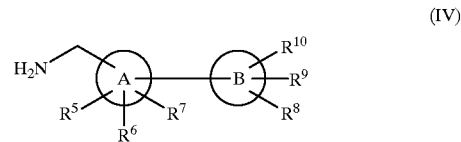

(IV)

(wherein R⁵, R⁶, R⁷, R⁸, R⁹, R¹⁰, A and B are defined as set forth above)
which comprises reducing a biaryl nitrile of formula (V)

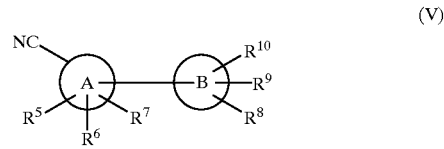

(V)

(wherein R⁵, R⁶, R⁷, R⁸, R⁹, R¹⁰, A and B are defined as set forth above)
by hydrogenation in the presence of a first catalyst, with or without an additive.

The biaryl nitrile of formula (V) is prepared by alkylating a nitrile of the formula (VI):

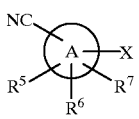

(VI)

(wherein $R^5$, $R^6$, $R^7$ and A are defined as set forth above; X is selected from halogen, sulfonate or phosphate) with a compound of the formula (VII):

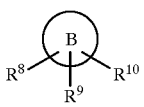

(VII)

(wherein $R^8$, $R^9$, $R^{10}$ and B are defined as set forth above) in the presence of a base, with or without a Lewis acid.

The nitrile of formula (VI) can be prepared by one of three methods:
(1) dehydrating an amide of the formula (VIII):

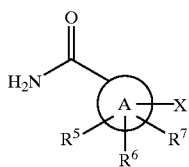

(VIII)

(wherein $R^5$, $R^6$, $R^7$ and A are defined as set forth above; X is selected from halogen, sulfonate or phosphate) by treating the amide with an inorganic acid halide, organic acid halide, or other active halogenating agent; or
(2) diazotizing an amine of the formula IX:

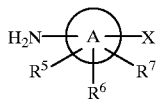

(IX)

(wherein $R^5$, $R^6$, $R^7$ and A are defined as set forth above; X is selected from halogen, sulfonate or phosphate) with a nitrite in the presence of an acid followed by treatment with a first metallic cyanide; or
(3) treating a compound of the formula (Xa):

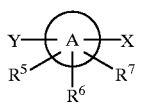

(Xa)

wherein $R^5$, $R^6$, $R^7$ and A are defined as set forth above; X is selected from halogen, sulfonate or phosphate; Y is selected from halogen, sulfonate or phosphate and Y is more reactive than X tow rds a second metallic cyanide, with or without a second catalyst)
with a second metallic cyanide, with or without a second catalyst.

First catalysts suitable for the reduction of the biaryl nitrile of formula (V) include: noble metals such as Pd, Rh, Ru, Pt, Mo, Ir and various salts, oxides, hydroxides and organometallic derivatives thereof; transition metals such as Ni, Co, Fe, Cu, Cr, Mn, B and various salts, hydroxides, oxides and organometallic derivatives thereof as well as other complex oxides such as copper chromite. Preferred first catalysts for this step include: Ni, Pd, Pt, Rh, Co and Mo. The most preferred first catalysts for this step include: Ni, Pd and Co.

Additives suitable for the reduction of the biaryl nitrile of formula (V) include: ammonia, ammonium hydroxide, NaOH, KOH, HCl or other additives commonly used in the hydrogenation of nitriles.

The source of hydrogen suitable for the hydrogenation of biaryl nitrile of formula (V) includes: $H_2$ or a suitable hydrogen transfer agent such as 1,4 cyclohexadiene or a formate salt.

A suitable temperature range for the reduction of the biaryl nitrile of formula (V) is about −80 to about 350° C., with a preferred temperature range being about 0 to about 140° C. and the most preferred temperature range being about 20 to about 90° C.

Reduction of the biaryl nitrile of formula (V) may be run neat. However, suitable solvents for the reduction include: water; alcohols such as MeOH, EtOH, n-PrOH, i-PrOH, butanols and alkoxyethanols; esters such as EtOAc, IPAC and BuOAc; hydrocarbons such as toluene or xylenes; chlorinated hydrocarbons such as dichloromethane, dichloroethane, chloroform, chlorobenzene and ODCB; ketones such as acetone, MEK, MIBK and cyclohexanone; ethers such as diethyl ether, MTE, THF, DME and DEM; other polar aprotic solvents such as formamide, DMF, DMA, NMP, DMPU, DMSO, and sulfolane or mixtures thereof. Preferred solvents for this step include: alcohols such as MeOH, EtOH, n-PrOH, i-PrOH, butanols and alkoxyethanols; ethers such as diethyl ether, MTBE, THF, DME and DEM; esters such as EtOAc, IPAC and BuOAc; other pollar aprotic solvents such as formamide, DMF, DMA, NMP, DMPU, DMSO, and sulfolane. The most preferred solvents for this step include: alcohols such as MeOH, EtOH, n-PrOH, i-PrOH; and THF.

Bases suitable for the alkylation of the nitrile of formula (VI) include: $Et_3N$, DIEA, n-$Bu_3N$, Imidazole, N-Me-imidazole, Pyridine, 2,6-Lutidine, 2,4,6-Collidine, 2,6-t$Bu_2$-pyridine, 2,6-t$Bu_2$-4-Me-pyridine, DMAP, DBU, DBN, DABCO, N-Me-morpholine, N-Et-morpholine, 1,2,2,6,6-$Me_5$-piperidine, $Me_4$-guanidine, Proton Sponge, N,N-$Me_2$-aniline, N,N-$Et_2$-aniline, Quinoline, i-$Pr_2$NH, Cyclohex$_2$NH, (Cyclohex)iPrNH, Pyrrolidine, Piperidine, 2,2,6,6-$Me_4$-piperidine, $TMS_2$NH (HMDS), $LiNH_2$, $NaNH_2$, $H_2$, LHMDS, NaHMDS, KHMDS, BnN$Me_3$OMe, NaOEt, TlOEt, LiOt-Bu, NaOt-Bu, KOt-Bu, LiOt-Am, NaOt-Am, KOt-Am, KH, KOTMS, NaH, KOH, n-$Bu_4$NOH, Triton-B, $Ca(OH)_2$, CaO, BaO, $Li_2CO_3$, $Na_2CO_3$, $K_2CO_3$, $Cs_2CO_3$, $(NH_4)_2CO_3$, Guanidine carbonate, $CaCO_3$, $NaHCO_3$, $KHCO_3$, and $K_3PO_4$. Preferred bases for this step include: $Li_2CO_3$, $Na_2CO_3$, $K_2CO_3$, $Cs_2CO_3$, DBU, DBN and $Me_4$-guanidine. The most preferred bases for this step include $Cs_2CO_3$ and $Me_4$-guanidine.

Lewis acid additives suitable for alkylation of the nitrile of formula (VI) include: metal halides, metal triflates, metal tetrafluoroborates, metal hexafluorophosphates, metal hexafluoroantimonates, or metal sulfates. The most preferred Lewis acid additive for this step is $Cu(OTf)_2$ with metallic Cu.

A suitable temperature range for alkylation of the nitrile of formula (VI) is about −80 to about 350° C., with a preferred temperature range being about 0 to about 140° C. and the most preferred temperature range being about 50 to about 90° C.

Alkylation of the nitrile of formula (VI) may be run neat. However, suitable solvents for the alkylation include: water; alcohols such as MeOH, EtOH, n-PrOH, i-PrOH, butanols and alkoxyethanols; esters such as EtOAc, IPAC and BuOAc; hydrocarbons such as toluene or xylenes; chlorinated hydrocarbons such as dichloromethane, dichloroethane, chloroform, chlorobenzene and ODCB; nitriles such as acetonitrile, propionitrile, benzonitrile and tolunitrile; ketones such as acetone, MEK, MIBK and cyclohexanone; ethers such as diethyl ether, MTBE, THF, DME and DEM; other polar aprotic solvents such as formamide, DMF, DMA, NMP, DMPU, DMSO, and sulfolane or mixtures thereof. Preferred solvents for this step include: alcohols such as MeOH, EtOH, n-PrOH, i-PrOH, butanols and alkoxyethanols; nitriles such as acetonitrile, propionitrile, benzonitrile and tolunitrile; ethers such as diethyl ether, MIBE, THF, DME and DEM; other polar aprotic solvents such as formamide, DMF, DMA, NMP, DMPU, DMSO, and sulfolane. The most preferred solvents for this step include: Acetonitrile, THF and DMF.

Inorganic acid halides suitable for dehydrating the amide of formula (VIII) include: $SOCl_2$, $SO_2Cl_2$, $S_2Cl_2$, $PCl_3$, $PCl_5$, $POCl_3$, $PSCl_3$, other mono or dihalophosphites [$(RO)_2$PCl or $ROPCl_2$], other mono or dihalophosphates [$(RO)_2$POCl or $ROPOCl_2$], other mono or dihalophosphines [$R_2PCl$ or $RPCl_2$], other mono or dihalophosphine oxides [$R_2POCl$ or $RPOCl_2$], $SiCl_4$, $SnCl_4$, and other metl or non-metal halides. The most preferred inorganic acid halides for this step include $SOCl_2$ and $POCl_3$.

Organic acid halides suitable for dehydrating the amide of formula (VIII) include: oxalyl chloride, acetyl chloride, phosgene, di and tri-phosgene, the chloroformates, the carbamoyl chlorides and the sulfonyl chlorides such as mesyl chloride or tosyl chloride. Preferred organic acid halides for this step are oxalyl chloride and mesyl chloride The most preferred organic acid halide for this step is oxlyl chloride.

Other active halogenating agents suitable four dehydrating the amide of formula (VIII) include: cyanouric chloride, Vilsmeier areagent, Phosgenimine, Gold's reagent, chlorinated heterocycles and combinations of halogenating agents, such as halogens, $CCl_4$, $C_2Cl_6$, or other alkyl halides, with reducing agents, such as triaryl or tialkyl phosphines or phosphites and a hydrogen halide, in the presence of a dehydrating agent. Preferred other active halogenating agents for this step include cyanouric chloride and Vilsmeier reagent. The most preferred other active halogenating agent for this step is Vilsmeier reagent.

A suitable temperature range for dehydration of the amide of formula (VIII) is about −50 to about 250° C., with a preferred temperature range being about −20 to about 100° C. and the most preferred temperature range being about 10 to about 90° C.

Dehydration of the amide of formula (VIII) may be run neat. However, suitable solvents for the dehydration include: hydrocarbons such as toluene or xylenes; chlorinated hydrocarbons such as dichloromethane, dichloroethane, chloroform, chlorobenzene and ODCB; nitriles such as acetonitrile, propionitrile, benzonitrile and tolunitrile; esters such as EtOAc, IPAC and BuOAc; ketones such as acetone, MEK, MIBK and cyclohexanone; ethers such as diethyl ether, MTBE, THF, DME and DEM; other polar aprotic solvents such as formamide, DMF, DMA, NMP, DMPU, DMSO, and sulfolane or mixtures thereof. Preferred solvents for this step include: hydrocarbons such as toluene or xylenes; chlorinated hydrocarbons such as dichloromethane, chloroform, chlorobenzene and ODCB; nitriles such as acetonitrile, propionitrile, benzonitrile and tolunitrile; esters such as EtOAc, IPAC and BuOAc; other polar aprotic solvents such as formamide, DMF, DMA, NMP, DMPU, DMSO, and sulfolane or mixtures thereof. The most preferred solvents for this step include: toluene, acetonitrile or DMF or mixtures thereof.

Nitrites suitable for the diazotization of the ainine of formula (IX) include: $NaNO_2$, $KNO_2$ and alkyl nitrites (RONO).

Acids suitable for the diazotization of the amine of formula (IX) include: HCl, HBr, HI, sulfuric, phosphoric, MsOH, TsOH, ammonium halides, phosphate salts and carboxylic acids such as HOAc and TFA. Preferred acids for this step include: HCl, HOAc, MsOH and sulfuric.

First metallic cyanides suitable for diazotization of the amine of formula (IX) include: CuCN, $Zn(CN)_2$, NaCN and KCN. Preferred first metallic cyanides for this step include: CuCN and $Zn(CN)_2$.

A suitable temperature range for the diazotization of the amine of formula (IX) is about −20 to about 100° C., with a preferred temperature range being about −15 to about 50° C. and the most preferred temperature range being about −10 to about 30° C.

Diazotization of the amine of formula (IX) may be run neat. However, suitable solvents for this step include: water; alcohols such as MeOH, EtOH, n-PrOH, i-PrOH, butanols and alkoxyethanols; esters such as EtOAc, IPAC and BuOAc; hydrocarbons such as toluene or xylenes; chlorinated hydrocarbons such as dichloromethane, dichloroethane, chloroform, chlorobenzene and ODCB; nitriles such as acetonitrile, propionitrile, benzonitrile and tolunitrile; ketones such as acetone, MEK, MIBK and cyclohexanone; ethers such as diethyl ether, MTBE, THF, DME and DEM; other polar aprotic solvents such as formamide, DMF, DMA, NMP, DMPU, DMSO, and sulfolane or mixtures thereof. Preferred solvents for this step include: $H_2O$ and HOAc.

Second metallic cyanides suitable for reaction with the compound of formula (Xa) include: CuCN, $Zn(CN)_2$, NaCN and KCN. Preferred second metallic cyanides for this step include: GuCN and $Zn(CN)_2$.

Second catalysts suitable for reaction with the compound of formula (Xa) include: Ni, Pd. Pt and the salts or complexes thereof such as halides, carboxylates, sulfonates and sigma donor complexes of the salts or metals. Preferred second catalysts for this step include: $PdCl_2$, $Pd(OAc)_2$, $Pd(PPh_3)_4$, $Pd(Ph_3)_2Cl_2$, $Pd_2(dba)_3$, $Ni(PPh_3)_2Cl_2$ and $Ni(Ph_3)_4$.

A suitable temperature range for the reaction with the compound of formula (Xa) is about −20 to about 250° C., with a preferred temperature range being about 0 to about 200° C. and the most preferred temperature range being about 20 to about 180° C.

The reaction of the compound (Xa) may be run neat. However, suitable solvents for this step include: water; alcohols such as MeOH, EtOH, n-PrOH, i-PrOH, butanols and alkoxyethanols; esters such as EtOAc, IPAC and BuOAc; hydrocarbons such as toluene or xylenes; chlorinated hydrocarbons such as dichloromethane, dichloroethane, chloroform, chlorobenzene and ODCB; nitriles such as acetonitrile, propionitrile, benzonitrile and tolunitrile; ketones such as acetone, MEK, MIBK and cyclohexanone; ethers such as diethyl ether, MTBE, THF, DME and DEM; other polar aprotic solvents such as formamide, DMF, DMA, NMP, DMPU, DMSO, and sulfolane or mixtures thereof Preferred solvents for this step include: NMP, DMF and DMPU.

Another embodiment of the instant invention involves the preparation of a compound of the formula (III) which is useful as an intermediate in the preparation of compounds of formula (I):

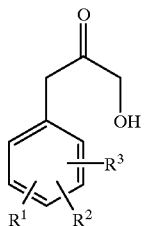

(III)

(wherein $R^1$, $R^2$ and $R^3$ are defined as set forth above)

which comprises hydrolyzing a vinyl sulfide of formula (XI):

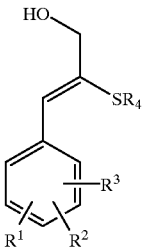

(XI)

(wherein $R^1$, $R^2$ and $R^3$ are defined as set forth above; R4 is selected from substituted or unsubstituted alkyl and substituted or unsubstituted aryl)

in the presence of an acid or a first transition metal or combination thereof The vinyl sulfide of formula (XI) is prepared by treating an alkyne of the formula (XII).

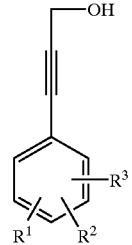

(XII)

(wherein $R^1$, $R^2$ and $R^3$ are defined as set forth above)

with a thiol in the presence of a first base. The alkyne of formula (XII) is prepared by treating a compound of the formula (XIII):

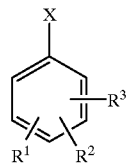

(XIII)

(wherein $R^1$, $R^2$ and $R^3$ are defined as set forth above; X is independently selected from: halogen, sulfonate and phosphate)
with propargyl alcohol in the presence of a second transition metal catalyst and a second base.

Acids suitable for hydrolyzing the vinyl sulfide of the formula (XI) include: HCl, HBr, HI, sulfuric, phosphoric, MsOH, TsOH, ammonium halides, phosphate salts and carboxylic acids such as HOAc and TFA. The most preferred acids for this step include: sulfuric, phosphoric, MsOH, TsOH and HCl.

First transition metals suitable for hydrolyzing the vinyl sulfide of formula (XI) include: Cu, Ni, Co, Fe, Mn, Cr, V, Ti, Sc, Y, Zr, Nb, Mo, Ru, Rh, Pd, Ag, Cd, La, Hf, Ta, W, Re, Os, Ir, Pt, Au, Zn, Hg and donor complexes thereof such as the phosphine complexes and various salts, hydroxides, oxides, and organometallic derivatives thereof such as the halides, carboxylates, triflates, tetrafluoroborates, hexafluorophosphates, hexafluoroantimonates, or sulfates and phosphine derivatives thereof and other Lewis Acids.

Combinations of the above transition metals and their derivatives with the above acids or various bases such as alkali or alkaline earth metal hydroxides, oxides, and carbonates are also suitable for hydrolyzing the vinyl sulfide of formula (XI).

A suitable temperature range for hydrolyzing the vinyl sulfide of formula (XI) is about −75 to about 200° C., with a preferred temperature range being about 0 to about 100° C. and the most preferred temperature range being about 40 to about 80° C.

Hydrolysis of the vinyl sulfide of formula (XI) may be run neat. However, solvents suitable for the hydrolysis include: water; alcohols such as MeOH, EtOH, n-PrOH, i-PrOH, butanols and alkoxyethanols; esters such as EtOAc, IPAC and BuOAc; hydrocarbons such as toluene or xylenes; chlorinated hydrocarbons such as dichloromethane, dichloroethane, chloroform, chlorobenzene and ODCB; nitriles such as acetonitrile, propionitrile, benzonitrile and tolunitrile; ketones such as acetone, MEK, MIBK and cyclohexanone; ethers such as diethyl ether, AMBE, THF and DME; other polar aprotic solvents such as formamide, DMF, DMA, NMP, DMPU, DMSO, and sulfolane or mixtures thereof. Preferred solvents for this step include: water; alcohols such as MeOH, EtOH, n-PrOH and i-PrOH; THF, DME, acetonitrile, formamide, DMF, DMA, NMP, DMPU, DNMSO, and sulfolane. The most preferred solvents for this step include: water; alcohols such as MeOH, EtOH, n-PrOH and i-PrOH; THE, DME and acetonitrile.

Thiols suitable for reaction with the alkyne of formula (XII) include: alkyl and aryl thiols such as: MeSH, EtSH, t-BuSH, n-BuSH, BnSH, PhSH, p-Thiocresol, $HSCH_2COOH$, $HSCH_2COOMe$ and $HSCH_2COOEt$. The most preferred thiols for this step include: EtSH, t-BuSH, BnSH, PhSH, n-BuSH and p-Thiocresol.

First bases suitable for reaction with the alkyne of formula (XII) include: $Et_3N$, DIEA, n-$Bu_3N$, Imidazole, N-Me-imidazole, Pyridine, 2,6-Lutidine, 2,4,6-Collidine, 2,6-$tBu_2$- pyridine, 2,6-tBu$_2$-4-Me-pyridine, DMAP, DBU, DBN, DABCO, N-Me-morpholine, N-Et-morpholine, 1,2,2,6,6-Me$_5$-piperidine, Me$_4$-guanidine, Proton Sponge, N,N-Me$_2$-aniline, N,N-Et$_2$-aniline, Quinoline, i-Pr$_2$NH, CYclohex$_2$NH, (Cyclohex)iPrNH, Pyrrolidine, Piperidine, 2,2,6,6-Me$_4$-piperidine, TMS$_2$NH (HMDS), LiNH$_2$, NaNH$_2$, KNH$_2$, LHMDS, NaHMDS, KHMDS, BnNMe$_3$OMe, NaOEt, TlOEt, LiOt-Bu, NaOt-Bu, KOt-Bu, LiOt-Am, NaOt-Am, KOt-Am, KH, KOTMS, NaH, LiOH, NaOH, KOH, n-Bu$_4$NOH, Triton-B, Ca(OH)$_2$, CaO, BaO, Li$_2$CO$_3$, Na$_2$CO$_3$, K$_2$CO$_3$, Cs$_2$CO$_3$, (NH$_4$)$_2$CO$_3$, Guanidine carbonate, CaCO$_3$, NaHCO$_3$, KHCO$_3$, K$_3$PO$_4$, EtNH$_2$, n-PrNH$_2$, n-BuNH$_2$, t-BuNH$_2$ and CyclohexylNH$_2$. Preferred first bases for this step include: Et$_3$N, DIEA, NaH, LiOH, NaOH and KOH. The most preferred first bases for this step include: LiOH, NaOH and KOH.

A suitable temperature range for the reaction with alkyne of formula (XII) is about −80 to about 350° C., with a preferred temperature range being about 0 to about 140° C. and the most preferred temperature range being about 0 to about 70° C.

The reaction of the alkyne of formula (XII) may be run neat. However, solvents suitable for this step include: water; alcohols such as MeOH, EtOH, n-PrOH, i-PrOH, butanols and alkoxyethanols; esters such as EtOAc, IPAC and BuOAc; hydrocarbons such as toluene or xylenes; chlorinated hydrocarbons such as dichloromethane, dichloroethane, chloroform, chlorobenzene and ODCB; nitriles such as acetonitrile, piropionitrile, benzonitrile and tolunitrile; ketones such as acetone, MEK, MIBK and cyclohexanone; ethers such as diethyl ether, MTBE, THF, DME and DEM; other polar aprotic solvents such as formamide, DMF, DMA, NMP, DMPU, DMSO, and sulfolane or mixtures thereof. Preferred solvents for this step include: hydrocarbons such as toluene or xylenes; nitriles such as acetonitrile, piropionitrile, benzonitrile and tolunitrile; ethers such as diethyl ether, MTBE, THF, DME and DEM; other polar aprotic solvents such as formamide, DMF, DMA, NMP, DMPU, DMSO, and sulfolane. The most pre,erred solvents for this step include: ethers such as diethyl ether, MTBE, THF, DME and DEM; nitriles such as acetonitrile, propionitrile, benzonitrile and tolunitrile.

Second transition metal catalysts suitable for reaction with compounds of formula (XIII) include: Cu, Ni, Co, Fe, Mn, Cr, V, Ti, Sc, Y, Zr, Nb, Mo, Ru, Rh, Pd, Ag, Cd, La, Hf, Ta, W, Re, Os, Ir, Pt, Au, Hg and donor complexes thereof such as the phosphine complexes and various salts, hydroxides, oxides, and organometallic derivatives thereof such as the halides, carboxylates, triflates, tetrafluoroborates, hexafluorophosphates, hexafluoroantimonates, or sulfates and phosphine derivatives thereof. Combinations of the above second transition metal catalysts are also suitable for reaction with compounds of the formula (XIII).

Second bases suitable for reaction with compounds of formula (XIII) include: Et$_3$N, DIEA, n-Bu$_3$N, Imidazole, N-Me-imidazole, Pyridine, 2,6-Lutidine, 2,4,6-Collidine, 2,6-tBu$_2$-pyridine, 2,6-tBu$_2$-4-Me-pyridine, DMAP, DBU, DBN, DABCO, N-Me-morpholine, N-Et-morpholine, 1,2,2,6,6-Me$_5$-piperidine, Me$_4$-guanidine, Proton Sponge, N,N-Me$_2$-aniline, N,N-Et$_2$-aniline, Quinoline, i-Pr$_2$NH, Cyclohex$_2$NH, (Cyclohex)iPrNH, Pyrrolidine, Piperidine, 2,2,6,6-Me$_4$-piperidine, TMS$_2$NH (HMDS), LiNH$_2$, NaNH$_2$, KNH$_2$, LHMDS, NaHMDS, KHMDS, BnNMe$_3$OMe, NaOEt, TlOEt, LiOt-Bu, NaOt-Bu, KOt-Bu, LiOt-Am, NaOt-Am, KOt-Am, KH, KOTMS, NaH, KOH, n-Bu$_4$NOH, Triton-B, Ca(OH)$_2$, CaO, BaO, Li$_2$CO$_3$, Na$_2$CO$_3$, K$_2$CO$_3$, Cs$_2$CO$_3$, (NH$_4$)$_2$CO$_3$, Guanidine carbonate, CaCO$_3$, NaHCO$_3$, KHCO$_3$, K$_3$PO$_4$, EtNH$_2$, n-PrNH$_2$, n-BuNH$_2$, t-BuNH$_2$ and CyclohexylNH$_2$. Preferred second bases for this step include: Et$_3$N, DIEA, n-Bu$_3$N, Imidazole, N-Me-imidazole, Pyridine, 2,6-Lutidine, i-Pr$_2$NH, Cyclohex$_2$NH, (Cyclohex)iPrNH, Pyrrolidine, Piperidine, Me$_4$-guanidine, EtNH$_2$, n-PrN$_2$, n-BuNH$_2$, t-BuNH$_2$ and CyclohexylNH$_2$. The most preferred second bases for this step include n-PrNH$_2$, n-BuNH$_2$ and t-BuNH$_2$.

A suitable temperature range for the reaction with compound (XIII) is about −80 to about 350° C., with a preferred temperature range being about 0 to about 140° C. and the most preferred temperature range being about 0 to about 70° C.

The reaction with compound (XIII) may be run neat. However, solvents suitable for this step include: water; alcohols such as MeOH, EtOH, n-PrOH, i-PrOH, butanols and alkoxyethanols; esters such as EtOAc, IPAC and BuOAc; hydrocarbons such as toluene or xylenes; chlorinated hydrocarbons such as dichloromethane, dichloroethane, chloroform, chlorobenzene and ODCB; nitriles such as acetonitrile, propionitrile, benzonitrile and tolunitrile; ketones such as acetone, MEK, MIBK and cyclohexanone; ethers such as diethyl ether, MTBE, TEHF, DME and DEM; other polar aprotic solvents such as formamide, DMF, DMA, NMP, DMPU, DMSO, and sulfolane or mixtures thereof. Preferred solvents for this step include: hydrocarbons such as toluene or xylenes; nitriles such as acetonitrile, propionitrile, benzonitrile and tolunitrile; ethers such as diethyl ether, MTBE, THF, DME and DEM; other polar aprotic solvents such as formamide, DMF, DMA, NMP, DMPU, DMSO, and sulfolane. The most preferred solvents for this step include ethers such as diethyl ether, MTBE, THF, DME and DEM.

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bond. Examples of alkynyl groups include acetylene, 2-butynyl, 2-pentynyl, 3-pentynyl and the like.

"Halogen" or "halo" as used herein means fluoro, chloro, bromo and iodo.

As used herein, "aryl," and the aryl portion of aroyl and aralkyl, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, althryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and 4,5,6,7-tetrahydro-3H-imidazo[4,5-c]pyridin-4-yl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^5$, $R^6$, $R^7$, $R^8$, $R^9$ and $R^{10}$ the term "the substituted group" is intended to mean a substituted $C_{1-8}$ alkyl, substituted aryl or substituted heterocycle from which the substituent(s) $R^5$, $R^6$, $R^7$, $R^8$, $R^9$ and $R^{10}$ are selected.

As used herein, when no specific substituents are set forth, the terms "substituted aryl", "substituted heterocycle" and "substituted cycloalkyl" are intended to include the cyclic group which is substituted on a substitutable ring carbon atom with 1 or 2 substituents selected from the group which includes but is not limited to F, Cl, Br, $CF_3$, $NH_2$, $N(C_1-C_6$ alkyl$)_2$, $(C_1-C_6$ alkyl)O—, —OH, $NO_2$, CN, $N_3$, $(C_1-C_6$ alkyl)S(O)$_m$—, $(C_1-C_6$ alkyl)C(O)NH—, $H_2N$—C(NH)—, $(C_1-C_6$ alkyl)C(O)—, $(C_1-C_6$ alkyl)OC(O)—, $(C_1-C_6$ alkyl)OC(O)NH—, phenyl, pyridyl, imidazolyl, oxazolyl, isoxazolyl, thiazolyl, thienyl, furyl, isothiazolyl and $C_1-C_{20}$ alkyl.

Preferably, the structure

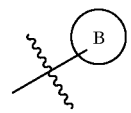

is selected from:

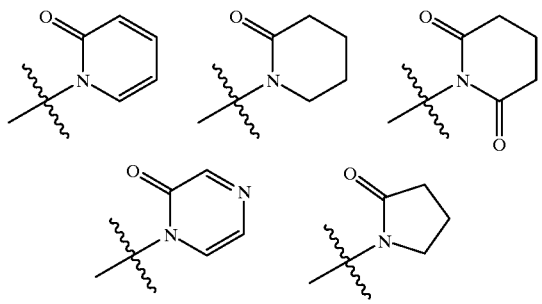

Most preferably, B is

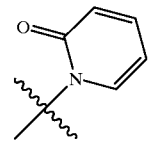

It is understood that such rings may be substituted by $R^8$, $R^9$ and/or $R^{10}$ as defined hereinabove.

Preferably A is the moiety designated by the following structure

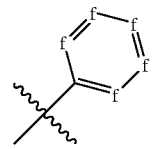

wherein f is independently selected from CH and N; which represents an aromatic 6-membered ring and includes the following ring systems:

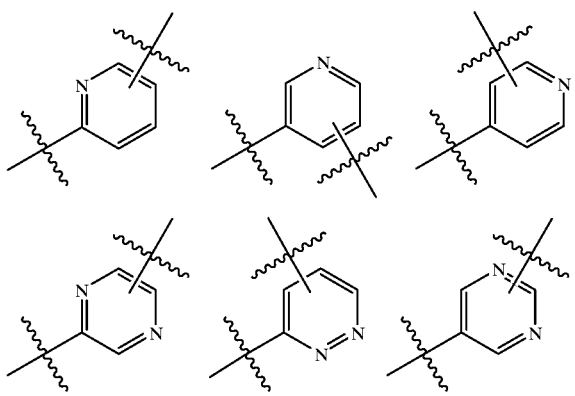

-continued

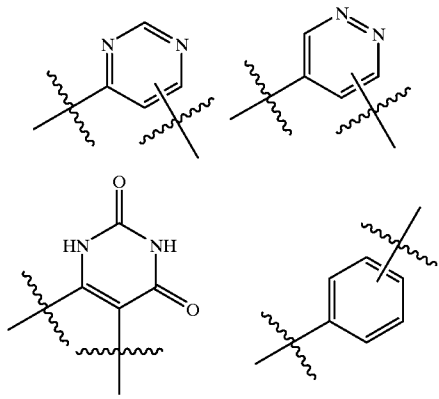

wherein it is understood that one of the ring carbon atoms is substituted with B. Preferably, A is selected from phenyl and pyridyl.

More preferably A is the moiety designated by the following structure

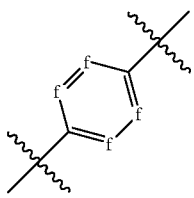

wherein f is independently selected from CH and N; which represents an aromatic 6-membered ring and includes the following ring systems:

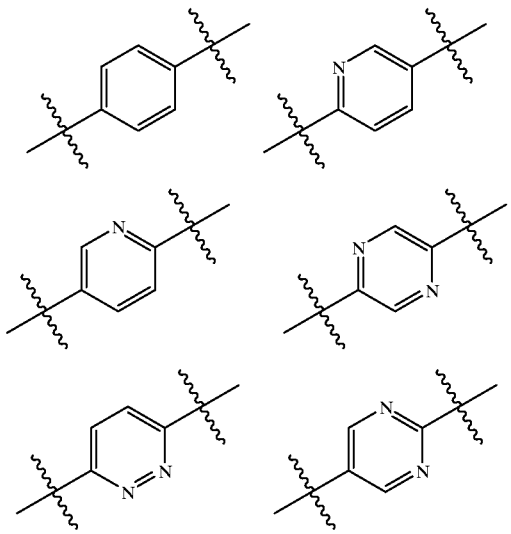

Preferably, A is selected from phenyl, pyrazine and pyridyl. Most preferably A is pyridyl.

Preferably, $R^1$ and $R^2$ are independently selected from:
a) hydrogen, and
b) aryl, substituted aryl, heterocycle, substituted heterocycle, $C_1$–$C_6$ perfluoroalkyl, $R^{11}O$— or CN.

More preferably $R^1$ is 4. CN and $R^2$ is hydrogen.

Preferably $R^3$ is hydrogen
Preferably, $R^5$ is selected from:
a) hydrogen,
b) $C_3$–$C_{10}$ cycloalkyl, halogen, $C_1$–$C_6$ perfluoroalkyl, $R^{13}O$—, $R^{11}C(O)$— or —$N(R^{11})_2$,
c) unsubstituted $C_1$–$C_6$ alkyl,
d) substituted $C_1$–$C_6$ alkyl wherein the substituent on the substituted $C_1$–$C_6$ alkyl is selected from unslibstituted or substituted aryl, unsubstituted or substituted heterocyclic, $C_3$–$C_{10}$ cycloalkyl, $R^{13}O$—, $R^{12}S(O)_m$—, $R^{11}C(O)NR^{11}$—, $(R^{11})_2NC(O)$—, $R^{11}{}_2N$—C($NR^{11}$)—, $R^{11}C(O)$—, —$N(R^{11})_2$, and $R^{12}OC(O)NR^{11}$—.

More preferably $R^5$ is hydrogen.
Preferably, $R^6$ is selected from: hydrogen, halogen, trifluoromethyl, trifluoromethoxy and $C_1$–$C_6$ alkyl. More preferably $R^6$ is hydrogen.

Preferably, $R^7$ is hydrogen.
Preferably, $R^8$, $R^9$ and $R^{10}$ are independently selected from:
a) hydrogen,
b) $C_3$–$C_{10}$ cycloalkyl, halogen, $C_1$–$C_6$ perfluoroalkyl, $R^{13}O$—, $R^{12}S(O)_m$—, $R^{11}C(O)$— or —$N(R^{11})_2$,
c) unsubstituted $C_1$–$C_6$ alkyl;
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $R^{13}O$—, $R^{12}S(O)_m$—, $R^{11}C(O)$— or —$N(R^{11})_2$.

More preferably $R^8$ is 5-Cl, $R^9$ is hydrogen and $R^{10}$ is hydrogen.

Preferably, $R^{11}$ is independently selected from hydrogen, $C_1$–$C_6$ alkyl, benzyl, 2,2,2-trifluoroethyl, aryl and substituted aryl. More preferably, $R^{11}$ is selected from H, $C_1$–$C_6$ alkyl and benzyl.

Abbreviations used throughout the specification include:

| | |
|---|---|
| ACN | Acetonitrile; |
| Bn | benzyl; |
| Bu | butyl; |
| Bu$_3$N | tributylamine; |
| BuOAc | butyl acetate; |
| Cu(OTf)$_2$ | copper (II) triflate; |
| cyclohex | cyclohexane; |
| DABCO | diazabicyclo[2.2.2]octane; |
| dba | trans, trans-dibenzylideneacetone; |
| DBU | 1,8-diazabicyclo[5.4.0]undec-7-ene; |
| DBN | 1,5-diazabicyclo[4.3.0]non-5-ene; |
| DEM | diethoxymethane; |
| DIEA | diisopropylethylamine; |
| DMA | N,N-dimethylacetamide; |
| DMAP | 4-Dimethylaminopyridine; |
| DME | 1,2-Dimethoxyethane; |
| DMF | dimethylformamide; |
| DMPU | 1,3-Dimethyl-3,4,5,6-tetrahydro-2-(1H)-pyrimidinone; |
| DMSO | dimethyl sulfoxide; |
| Et | ethyl; |
| Et$_3$N | triethylamine; |
| EtOAc | ethyl acetate; |
| HOAc | acetic acid; |
| IPAC | isopropyl acetate; |
| KHMDS | potassium bis(trimethylsilyl)amide; |
| KOt-Am | potassium tert-pentoxide; |
| KOTMS | potassium trimethylsilanolate; |
| LHMDS | lithium bis(trimethylsilyl)amide; |
| LiOt-Am | lithium tert-pentoxide; |
| Me | methyl; |
| MEK | methyl ethyl ketone; |
| MIBK | methyl isobutyl ketone; |
| MsOH | methanesulfonic acid; |

-continued

| | |
|---|---|
| MTBE | methyl-t-butyl-ether; |
| NaHMDS | sodium bis(trimethylsilyl)amide; |
| NaOt-Am | sodium tert-pentoxide; |
| NMP | N-Methyl pyrrolidinone; |
| ODCB | ortho Dichlorobenzene, or 1,2-dichlorobenzene; |
| Ph | phenyl; |
| Pr | propyl; |
| TFA | trifluoroacetic acid; |
| THF | tetrahydrofuran; |
| TMS$_2$NH | 1,1,1,3,3,3-hexamethyldisilazine; |
| HMDS | 1,1,1,3,3,3-hexamethyldisilazine; |
| TMS-SCN | trimethylsilyl cyanide; |
| TsOH | P-Toluenesulfonic acid. |

Scheme I provides further illustration of the reaction sequence of the instant invention.

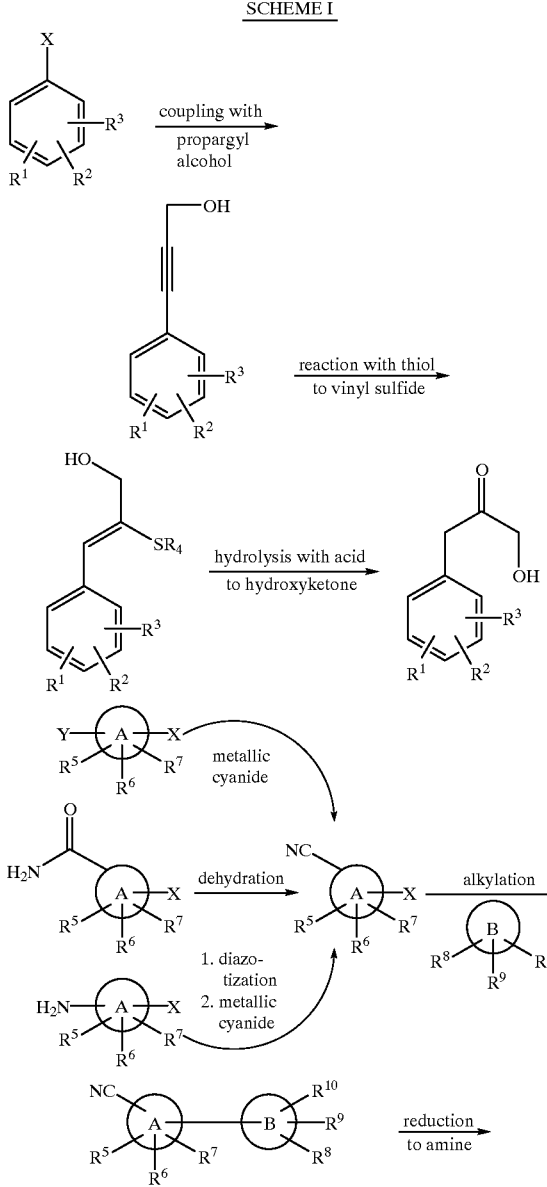

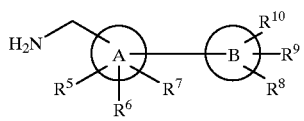

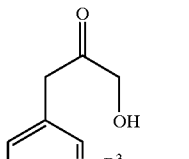

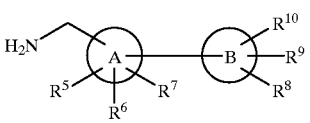

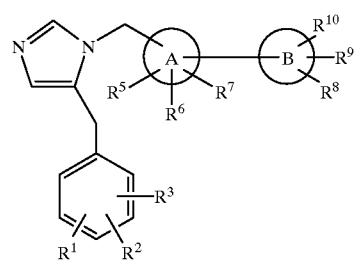

Wherein $R^1$, $R^2$, $R^3$, $R^5$, $R^6$, $R^7$, $R^8$, $R^9$, $R^{10}$, A, B, X and Y are defined as set forth above and $R^4$ is selected from substituted or unsubstituted alkyl and substituted or unsubstituted aryl.

A preferred embodiment of the present invention involves preparation of a compound of formula (10):

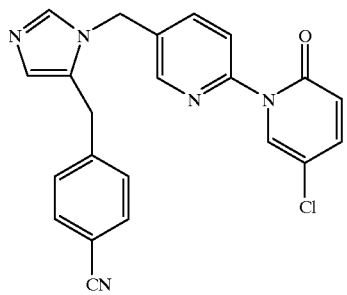

(10)

by the process set forth in Schemes II, III and IV:

SCHEME II

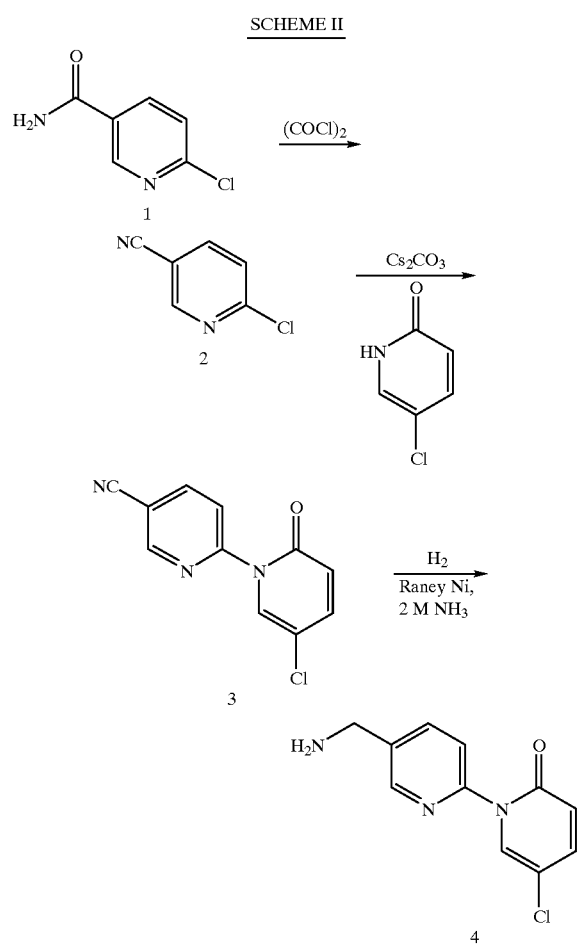

SCHEME III

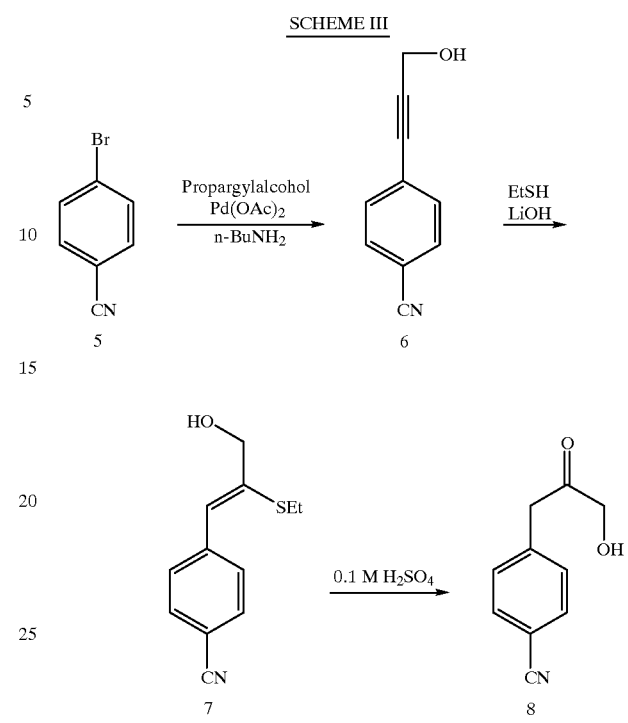

Treatment of chloronicotinamide 1 with a slight excess of oxalylchloride in DMF leads rapidly and cleanly to nitrile 2. $Na_2CO_3$ is added to the crude nitrile solution to scavenge the HCl. The insoluble salts are then filtered off. Alternatively, nitrile 2 can be synthesized from the corresponding amine, halide, sulfonate or phosphate. For example, nitrile 2 can be prepared by diazotization of the corresponding amine followed by treatment with a metallic cyanide such as CuCN, $Zn(CN)_2$, NaCN or KCN. Nitrile 2 can also be synthesized from the corresponding halide, sulfonate or phosphate by treatment with a metallic cyanide such as CuCN, $Zn(CN)_2$, NaCN or KCN, with or without a catalyst such as Ni, Pd or Pt.

Numerous reaction conditions were explored to convert nitrile 2 into 3. After overnight stirring with $K_2CO_3$ at 70° C. in DMF, an 85:15 mixture of the N- and O-alkylated pyridones is produced. Upon further examination of this reaction, it was found that the reactivity and the N/O-alkylation ratio increased as one proceeded down the Group IA metals. Based upon these discoveries, an optimized procedure was developed in which the nitrile 2 is dissolved in DMF and the pyridone and $Cs_2CO_3$ are added. After aging at 75° C., followed by crystallization with $H_2O$, cyanopyridone 3 is isolated.

The cyanopyridone 3 was reduced to benzylic amine 4, by hydrogenation at 40 psi, 50° C., Raney Ni, using 2 M $NH_3$ in 2-propanol. Reduction of the cyanopyridone 3 can also be achieved by hydrogenation at 40 psi, 25° C., Raney Ni, using aqueous ammonium hydroxide in MeOH and THF.

Coupling of 4, bromobenzonitrile 5 with propargyl alcohol in the presence of $Pd(OAc)_2$ and n-$BuNH_2$ gives alkyne 6.

Hydration of alkyne 6 to hydroxyketone 8 is achieved by a two step procedure. Thiols (EtSH, PhSH and n-BuSH for example) in the presence of $K_2CO_3$, LiOH, KOH or NaOH add smoothly and regioselectively in a [1,8] sense to alkyne 6, giving the corresponding vinyl sulfide 7. Hydrolysis of vinyl sulfide 7 to hydroxyketone 8 is realized with 0.1 M $H_2SO_4$ at 70–75° C.

SCHEME IV

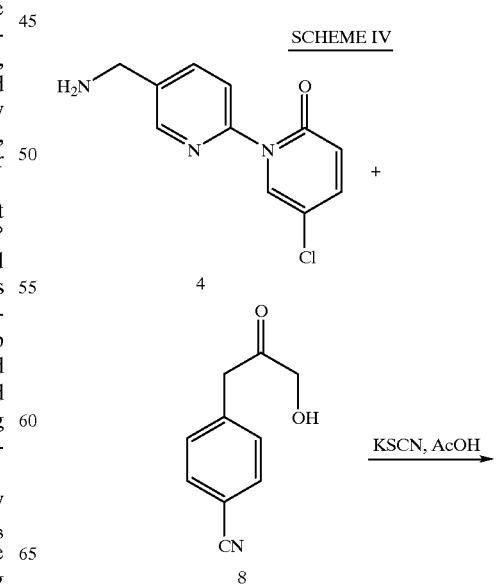

-continued

[Structure 9: thioimidazole with SH group, N-CH2-pyridine-pyridinone-Cl, and benzyl-CN substituent]

→ NaNO₂(aq) / AcOH →

[Structure 10: imidazole, N-CH2-pyridine-pyridinone-Cl, and benzyl-CN substituent]

Treatment of hydroxyketone 8 and benzylic amine 4 with KSCN and acetic acid in n-BuOH or an ACN/water mixture provides thioimidazole 9. Dethionation to imidazole 10 was achieved by adding an aqueous solution of $NaNO_2$ to an acetic acid solution of thioimidazole 9. Dethionation under these mild conditions gives a controlled exotherm and a controlled release of nitroger oxide gas.

EXAMPLES

The instant invention is further illustrated by the following examples:

Example 1

Preparation of Chloronitrile 2

[Structure 2: NC-pyridine-Cl]

A 1L 4 neck flask equipped with a mechanical stirrer was charged with 6-chloronicotinamide 1 (105 g, 672 mmol). $POCl_3$ (4 mL/g, 413 mL) was added and the solution was heated to 75° C. for 30 min then heated at 85° C. for 1 h. The excess $POCl_3$ was removed via vacuum distillation. The $POCl_3$ distilled at 45–55° C./20–25 torr. After most of the $POCl_3$ was removed, 100 mL of toluene was added and then removed by distillation. MeOH was added to the crude solid that remained in the flask. The mixture was stirred overnight yielding a white powdery suspension. NaOH (5N, 250 mL) was added until the pH was adjusted to 12. The reaction mixture was filtered. The product was dried under vacuum with a low flow of nitrogen yielding 91.4 g (98%) of a 6-chloronicotinonitrile 2.

Example 2

Preparation of Chloronitrile 2

[Structure 2: NC-pyridine-Cl]

6-Chloronicotinamide 1 (4.7 g, 30 mmol) was dissolved in 38 mL of DMF. Oxalyl chloride (2.7 mL, 30.3 mmol) was added dropwise over 10 min. There was a rapid evolution of CO and $CO_2$ and the temperature increased to 38° C. The solution was cooled to 0° C. and NaOH (5N, 15.5 mL) was added slowly. Water (125 mL) was added keeping the temperature below 10° C. The mixture was aged 2 h at 0° C. then filtered. The solid was washed with water (slurry (30 mL), displacement (20 mL)). The isolated yield was 3.33 g (80%) of 6-chloronicotinonitrile 2 (100% pure by HPLC).

Example 3

Preparation of Biaryl Nitrile 3

[Structure 3: NC-pyridine-N-pyridinone-Cl]

A mixture of chloronitrile 2 (20.1 g, 142 mmol), 5-chloro-2-pyridinol (20.6 g, 156 mmol), cesium carbonate (56.3 g, 170 mmol) and DMF (300 mL) was heated to 75° C. for 19 h. The mixture was cooled to 25° C. and diluted with water (300 mL). The precipitated product was filtered off, washed with water (1.5 L) and dried to provide biaryl nitrile 3 (29.3 g, 89%).

$^{13}C$ NMR (75.5 MHz, $CDCl_3$) δ 160.4, 152.9, 151.7, 141.7, 141.1, 131.9, 123.4, 120.7, 115.8, 114.3, 109.1. Anal. Calcd for $C_{11}H_6N_3OCl$: C, 57.04; H, 2.61; N, 18.14. Found: C, 56.87; H, 2.59; N, 18.08.

Example 4

Preparation of Benzylic Amine 4

[Structure 4: H2N-CH2-pyridine-N-pyridinone-Cl]

A mixture of biaryl nitrile 3 (0.51 g, 2.2 mmol), Raney nickel (0.16 g, EtOH washed wet), concentrated aqueous ammonium hydroxide (7 mL), MeOH (7 mL) and THF (7

Example 5

Preparation of Benzylic Amine 4

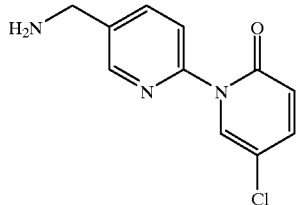

4

Raney nickel (1.00 g) was charge to a hydrogenation vessel and washed three times with IPA. To this same vessel was added 2.0 M $NH_3$ in IPA (80 mL) and the biaryl nitrile 3 (2.0 g, 8.6 mmol). The mixture was pressurized with $H_2$ (40 psi) and shaken while heating at 50° C. for 15 h. To the mixture was added $CH_2Cl_2$ until the organic solids dissolved. The solution was filtered through Celite, washing with $CH_2Cl_2$ and MeOH. The crude material was concentrated, then chromatographed on $SiO_2$ (1:1 $CH_2Cl_2$/MeOH), yielding 1.45 g (71%) of the desired benzylic amine 4.

$^{13}C$ NMR (75.5 MHz, $CDCl_3$) δ 160.6, 149.7, 147.7, 141.1, 138.4, 136.9, 133.5, 122.8, 120.7, 113.2, 43.2.

Example 6

Preparation of Propargylic Alcohol 6

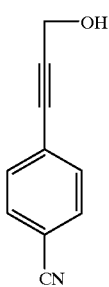

6

A 100 mL three-neck oven-dried flask with magnetic stir bar was purged with nitrogen, then charged with triphenyl phosphine (1.9994 g, 7.6 mmol), bromobenzonitrile 5 (9.2235 g, 50.7 mmol), copper iodide (0.624 g, 3.3 mmol), and palladium acetate (0.556 g, 2.5 mmol). THF (30 mL) was added and the solution purged with nitrogen. Butylamine (20 ml, 202.4 mmol) was added to form a clear, blue solution. To the room temperature solution, propargyl alcohol (3.554 g, 50.7 mmol) was slowly added by addition funnel over 15 minutes. After 4 hours, the reaction was complete by HPLC. The THF was removed under reduced pressure and the black oil purified on silica gel (50 g, hexane/ethyl acetate eluant). A pale yellow solid (4.01 g, 50.3%) was obtained.

Example 7

Preparation of Propargylic Alcohol 6

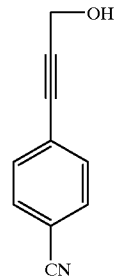

6

A 250 mL three-neck oven-dried flask with magnetic stir bar was purged with nitrogen, then charged with triphenyl phosphine (5.2230 g, 19.9 mmol), bromobenzonitrile 5 (18.51 g, 101.7 mmol), copper iodide (2.1843 g, 11.5 mmol), and palladium acetate (0.9114 g, 40 mmol). MTBE (100 mL) was added and the solution purged with nitrogen. Butylamine (20 ml, 202.4 mmol) was added to form a clear solution. The solution was warmed to 50° C., and propargyl alcohol (7.0 mL, 130.0 mmol) was slowly added by addition funnel over 30 minutes. The reaction was aged for 72 hours. HPLC showed complete conversion. The reaction was concentrated under reduced pressure and the residue passed through 100 g silica with MTBE. The filtrate was concentrated to dryness under reduced pressure to give a yellow solid. Toluene (100 mL) was added and the mixture heated to 60° C. to dissolve the solid. The solution was hot filtered through solkaflok and cooled to 10° C. Hexanes (50 mL) was added dropwise to form a yellow precipitate. The slurry aged for 1.5 hours at 10° C. The solid was collected by vacuum filtration, washed with cold 1:1 toluene/hexanes (2×40 mL) and hexanes (60 mL). The yellow solid was dried overnight under vacuum to provide the desired alkynol 6 (12.08 g, 76.9% yield).

Example 8

Preparation of Vinyl Sulfide 7

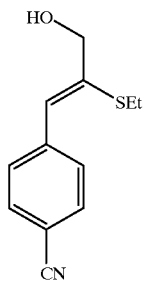

7

The alcohol 6 (1.02 g, 6.51 mmol) was dissolved in MeCN (3.5 mL) at 25° C. Ethanethiol (0.65 mL, 8.8 mmol) and LiOH monohydrate (0.23 g, 6.7 mmol) were added and the mixture was heate, to 60° C. for 1 h. The mixture was cooled to 25° C. and diluted with MeCN to a total volume of 10 mL and used in the next step without isolation. The HPLC assay yield was 84%.

Example 9

Preparation of Phenyl Vinyl Sulfide 7a

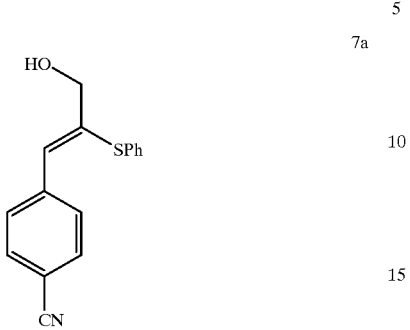
7a

The alcohol 6 (10.5 g, 66.7 mmol) was dissolved in MTBE (67 mL) at 25° C. Thiophenol (8.81 g, 80.0 mmol) and LiOH monohydrate (0.28 g, 6.7 mmol) were added and the mixture was heated to 50° C. for 3 h. The mixture was diluted with MTBE (50 mL), washed with brine (100 mL) and dried ($MgSO_4$). The organic extract was evaporated down to 50 mL volume and hexane (120 mL) was added gradually over 1 h at 20° C. The crystalline solid was filtered off, washed with hexane (60 mL) and dried to provide 2-thiophenyl-3-(4-cyanophenyl)-2-propene-1-ol (16.9 g, 95%).

Anal. Calcd for $C_{16}H_{13}NOS$: C, 71.88; H, 4.90; N, 5.24. Found: C, 71.88; H, 4.76; N, 5.20.

Example 10

Preparation of Butyl Vinyl Sulfide 7b

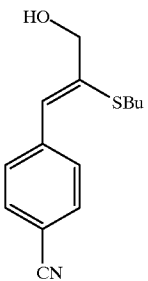
7b

The alcohol 6 (7.86 g, 50.0 mmol) and KOH (45%, 1.28 g, 10.2 mmol) were slurried in MeCN (50 mL) at 25° C. Butanethiol (7.0 mL, 65.4 mmol) was added by syringe over 30 minutes. A slight exotherm was noticed. After 1 hour, the mixture was concentrated under reduced pressure and the crude oil was adsorbed onto silica gel. The silica was washed with 50 mL hexanes, then 200 mL MTBE. The MTBE wash was concentrated under reduced pressure to afford the butyl vinyl sulfide (11.69 g, 94.5% yield) as a dark yellow oil.

Example 11

Preparation of Butyl Vinyl Sulfide 7b

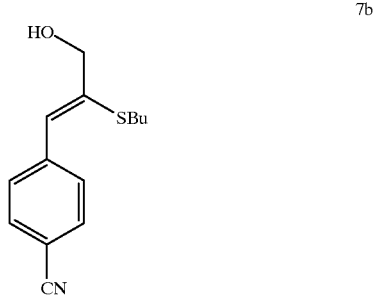
7b

The alcohol 6 (1.57 g, 10.0 mmol) and powdered NaOH (0.44 g, 11.0 mmol) were slurried in MeCN (10 mL) at 25° C. Butanethiol (1.2 mL, 11.2 mmol) was added by syringe over 10 minutes. A slight exotherm was noticed, with the temperature maintaines between 30–35° C. After 15 minutes, the mixture was concentrated under reduced pressure and the crude oil was purified on silica gel with 0.5 g of DARCO as the top layer using MTBE as the eluant. The MTBE filtrate was concentrated under reduced pressure to afford the vinyl sulfide (2.24 g, 90.7% yield) as an orange oil.

$^1$H NMR (300 MHz, $CDCl_3$): δ 7.67 (d, 2H), 7.68 (d, 2H), 6.78 (s, 1H), 4.37 (d, 2H), 2.80 (t, 2H), 2.13 (t, 1H), 1.53 (m, 2H), 1.36 (m, 2H), 0.87 (t, 3H).

The following additional compounds were prepared by the methods set forth in Example 11 by starting with the appropriate alcohol:

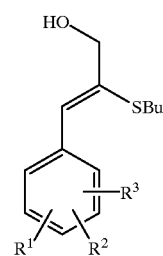

| $R_1$ | $R_2$ | $R_3$ | Time | Temp. | Yield |
|---|---|---|---|---|---|
| H | H | H | 3 hrs | 75° C. | 86% |
| 3-$CF_3$ | 5-$CF_3$ | H | .25 hrs | 20° C. | 98% |
| 4-OMe | H | H | 5 hrs | 75° C. | 86% |

Example 12

Preparation of Hydroxy Ketone 8

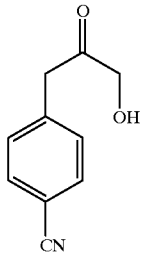

The crude MeCN solution from Example 8 (3.33 mL) containing 1.64 mmol of vinyl sulfide 7 was stirred with concentrated sulfuric acid (30 mL) and water (2 mL) for 1 h at 25° C. The mixture was heated to 70° C. for 18 h, cooled to 25° C. and diluted with brine (5 mL). The mixture was extracted with IPAC (4×10 mL) and the organic extracts were evaporated leaving 315 mg residue. The residue was purified by flash column chromatography on 25 g silica eluting with 2:1 EtOAc-hexane to provide hydroxyketone 8 (237 mg, 82% from 6).

$^{13}$C NMR (75.5 MHz, CDCl$_3$) δ 205.9, 138.1, 132.5, 130.3, 118.6, 111.3, 68.1, 45.1. Anal: Anal. Calcd for C$_{10}$H$_9$NO$_2$: C, 68.56; H, 5.18; N, 8.00. Found: C, 68.69; H, 5.04; N, 7.93.

Example 13

Preparation of Hydroxy Ketone 8

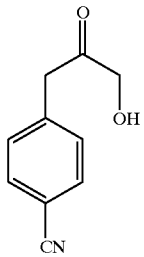

To a solution of the vinyl sulfide 7 (1.95 mmol) in 3 mL of acetonitrile was added 2 mL of water and 0.030 mL of concentrated H$_2$SO$_4$ (0.54 mmol). The reaction mixture was heated to 75° C. and stirred overnight. The solution was cooled to room temperature and 5 mL of aqueous saturated NaCl was added. The resulting mixture was extracted with IPAC (4×10 mL). The IPAC extracts were dried over MgSO$_4$, filtered and concentrated yielding 315 mg of the crude product. The crude product was purified by flash chromatography (25 g of silica gel) eluting with 2:1 EtOAc/hexane. The isolated yield was 237 mg (82% over 2 steps) of hydroxy ketone that is 99.8% pure by HPLC.

$^{13}$C NMR (75.5 MHz, CDCl$_3$) δ 205–9, 138.1, 132.5, 130.3, 118.6, 111.3, 68.1, 45.1.

Example 14

Preparation of Hydroxy Ketone 8

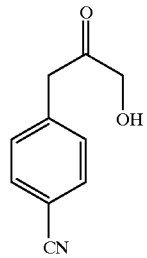

The crude vinyl sulfide 7b from Example 10 (11.69 g, 47.3 mmol) was diluted with 125 mL of ethanol (95%) and 35 mL of 1N H$_2$SO$_4$. The mixture was heated to 75° C. for 36 h, cooled to 25° C. and diluted with brine (100 mL). The mixture was extracted with EtOAc (160 mL) and the organic extracts were evaporated to a crude oil. The crude product was passed through a plug of silica with 100 mL EtOAc and the filtrates evaporated under reduced pressure to dryness. The crude oil was dissolved in 150 mL EtOAc and treated with 2 g DARCO. The slurry was aged 20 minutes, then filtered. The filtrate was evaporated to dryness. Toluene (50 mL) was added and the mixture warmed to dissolve the solids. Hexanes (100 mL) was added dropwise to crystallize the product. The slurry was cooled to 10° C. and the solid collected by vacuum filtration. The off-white solid was washed with cold 1:1 toluene/hexanes (50 mL) and cold hexanes (2×50 mL) and dried under vacuum to give the hydroxyketone 8 (7.02 g, 84.8% yield).

$^{13}$C NMR (75.5 MHz, CDCl$_3$) δ 205.9, 138.1, 132.5, 130.3, 118.6, 111.3, 68.1, 45.1.

Example 15

Preparation of Thioimidazole 9

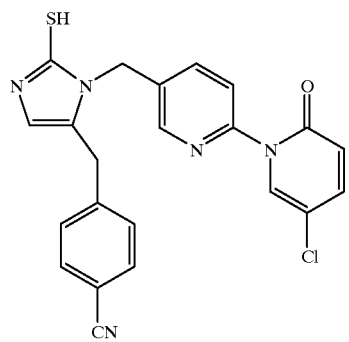

A mixture of hydroxyketone 8 (37 mg, 0.21 mmol), benzylic amine 4 (47 mg, 0.21 mmol), KSCN (25 mg, 0.25 mmol), HOAc (26 mg, 0.42 mmol) and n-butanol (1 mL) was heated to 50° C. for 18 h. The mixture was diluted with water (5 mL) and the precipitated solid product was filtered off.

$^1$H NMR (250 MHz, CDCl$_3$) δ 8.32 (s, 1H), 8.05 (d, J=3.7 Hz, 1H), 7.80 (m, 2H), 7.61 (d, J=6.9 Hz, 1H), 7.50 (dd, J=6.9, 1.9 Hz, 1H), 7.35 (d, J=6.9 Hz, 1H), 6.82 (s, 1H), 6.56 (d, J=8.1 Hz, 1H), 5.40 (s, 2H), 4.09 (s, 2H).

Example 16

Preparation of Thioimidazole 9

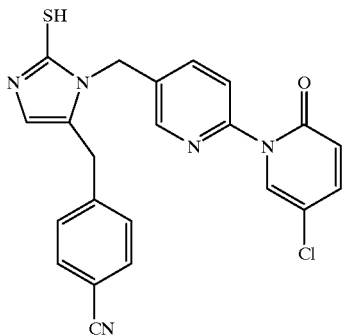

A mixture of hydroxyketone 8 (381 mg, 2.18 mmol), benzylic amine 4 (513 mg, 2.18 mmol), KSCN (263 mg, 2.70 mmol) HOAc (434 mg, 5.86 mmol) in 95:5 ACN/H$_2$O (2.7 mL) was heated to 70° C. for 2 h. ACN (2 mL) was added to the mixture and aged 1.5 h at 23° C. The mixture was cooled to 0° C., solid product was filtered off, washing with ACN (2×3 mL).

$^1$H NMR (250 MHz, CDCl$_3$) δ 8.32 (s, 1H), 8.05 (d, J=3.7 Hz, 1H), 7.80 (m, 2H), 7.61 (d, J=6.9 Hz, 1H), 7.50 (dd, J=6.9, 1.9 Hz, 1H), 7.35 (d, J=6.9 Hz, 1H), 6.82 (s, 1H), 6.56 (d, J=8.1 Hz, 1H), 5.40 (s, 2H), 4.09 (s, 2H).

Example 17

Preparation of Imidazole 10

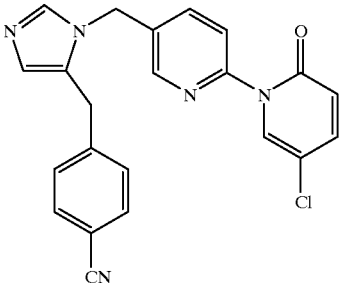

A 1.0M aqueous solution of sodium nitrite (1.96 mL, 1.96 mmol) was added to a suspension of thioimidazole 9 (213 mg, 0.49 mmol) in HOAc (4 mL) at 25° C. and the resulting yellow solution stirred for 18 h. The mixture was evaporated and the residue was triturated with dichloromethane (10 mL). The dichloromethane extract was filtered and evaporated leaving 202 mg residue. The residue was purified by flash column chromatography on 30 g silica eluting with 20:1 MeOH-dichloromethane to provide 10 (111 mg, 56% from 9).

$^{13}$C NMR (75.5 MHz, CDCl$_3$) δ 160.4, 151.0, 146.8, 142.9, 141.3, 138.1, 136.0, 132.6, 132.4, 131.2, 129.9, 128.8, 128.1, 123.0, 121.0, 118.1, 113.3, 110.8, 45.5, 30.2.

What is claimed is:

1. A process for the preparation of a compound of the formula (I):

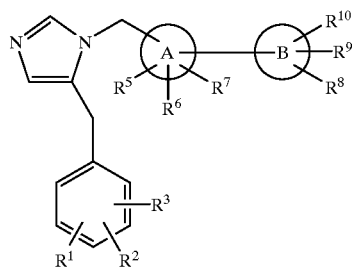

wherein:

$R^1$, $R^2$ and $R^3$ are independently selected from:
a) hydrogen,
b) aryl, substituted aryl, heterocycle, substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{11}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{11}_2N$—C(NR$^{11}$)—, CN, NO$_2$, $R^{11}C(O)$—, N$_3$, —N(R$^{11}$)$_2$, or $R^{12}OC(O)NR^{11}$—, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{11}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{11}_2N$—C(NR$^{11}$)—, CN, $R^{11}C(O)$—, N$_3$, —N(R$^{11}$)$_2$, or $R^{11}OC(O)NH$—;

$R^5$, $R^6$ and $R^7$ are independently selected from:
a) hydrogen,
b) unsubstituted or substituted aryl, unsubstituted or substituted heterocycle, $C_3$–$C_{10}$ cycloalkyl, halogen, $C_1$–$C_6$ perfluoroalkyl, $R^{13}O$—, $R^{12}S(O)_m$—, $R^{11}C(O)NR^{11}$—, $(R^{11})_2NC(O)$—, $R^{12}C(O)O$—, $R^{11}_2N$—C(NR$^{11}$)—, $R^{11}C(O)$—, —N(R$^{11}$)$_2$, or $R^{12}OC(O)NR^{11}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $R^{13}O$—, $R^{12}S(O)_m$—, $R^{11}C(O)NR^{11}$—, $(R^{11})_2NC(O)$—, $R^{11}_2N$—C(NR$^{11}$)—, $R^{11}C(O)$—, —N(R$^{11}$)$_2$, and $R^{12}OC(O)$—NR$^{11}$—;

$R^8$, $R^9$ and $R^{10}$ are independently selected from:
a) hydrogen,
b) unsubstituted or substituted aryl, unsubstituted or substituted heterocycle, $C_3$–$C_{10}$ cycloalkyl, halogen, $C_1$–$C_6$ perfluoroalkyl, $R^{13}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{12}C(O)O$—, $R^{11}_2N$—C(NR$^{11}$)—, $R^{11}C(O)$—, —N(R$^{11}$)$_2$, or $R^{12}OC(O)NR^{11}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $R^{13}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{11}_2N$—C(NR$^{11}$)—, $R^{11}C(O)$—, —N(R$^{11}$)$_2$, and $R^{12}OC(O)$—NR$^{11}$—; or any two of $R^8$, $R^9$ and $R^{10}$ on adjacent carbon atoms are combined to form a diradical selected from —CH═CH—CH═CH—, —CH═CH—CH$_2$—, —(CH$_2$)$_4$— and —(CH$_2$)$_3$—;

A is:
   a 5, 6 or 7 membered carbocyclic ring wherein from 0 to 3 carbon atoms are replaced by a heteroatom selected from N, S and O, and wherein A is attached to B through a carbon atom;

B is:
   a 4, 5, 6 or 7 membered heterocyclic ring which comprises a nitrogen atom through which B is attached to A and 0–2 additional heteroatoms selected from N, S an O, and which also comprises a carbonyl, thiocarbonyl, —C(=NR$^{14}$)— or sulfonyl moiety adjacent to the nitrogen atom attached to A;

R$^{11}$ is independently selected from hydrogen, C$_1$–C$_6$ alkyl amino-C$_1$–C$_6$ alkyl, N-(unsubstituted or substituted benzoyl)-amino-C$_1$–C$_6$ alkyl, (C$_1$–C$_6$ alkyl)$_2$-amino-C$_1$–C$_6$ alkyl, acetylamino-C$_1$–C$_6$ alkyl, phenyl-C$_1$–C$_6$ alkyl, 2,2,2-trifluoroethyl, aryl and substituted aryl;

R$^{12}$ is independently selected from C$_1$–C$_6$ alkyl and aryl;

R$^{13}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted heteraryl, C$_1$–C$_6$ perfluoroalkyl, 2-aminoethyl and 2,2,2-trifluoroethyl;

R$^{14}$ is selected from hydrogen, C$_1$–C$_6$ alkyl, C$_1$–C$_6$ alkylsulfonyl and C$_1$–C$_6$ acyl;

m is 0, 1 or 2;

which comprises dethionating a thioimidazole of the formula (II):

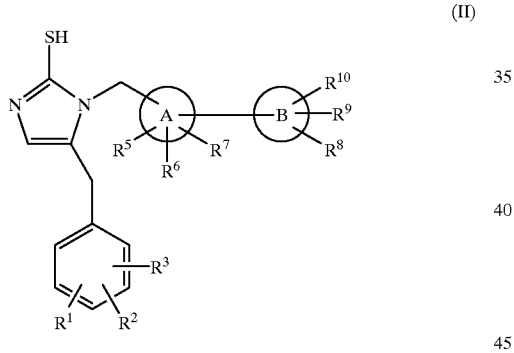

(II)

wherein R$^1$, R$^2$, R$^3$, R$^5$, R$^6$, R$^7$, R$^8$, R$^9$, R$^{10}$, A and B are defined as set forth above;
with an oxidizing agent in the presence of an acid.

2. The process according to claim 1, wherein the oxidizing agent is selected from: hydrogen peroxide and nitrous acid.

3. The process according to claim 2, wherein the oxidizing agent is aqueous NaNO$_2$ or aqueous KNO$_2$.

4. The process according to claim 1, wherein the acid is selected from: MsOH, HOAc and TFA.

5. The process according to claim 4, wherein the acid is HOAc.

6. The process according to claim 1 wherein:
   R$^1$ and R$^2$ are independently selected from:
      a) hydrogen, and
      b) aryl, substituted aryl, heterocycle, substitutes heterocycle, C$_1$–C$_6$ perfluoroalkyl, R$^{11}$O— or CN;
   R$^3$ is hydrogen;
   R$^5$ is selected from:
      a) hydrogen,
      b) C$_3$–C$_{10}$ cycloalkyl, halogen, C$_1$–C$_6$ perfluoroalkyl, R$^{13}$O—, R$^{11}$C(O)— or —N(R$^{11}$)$_2$,
      c) unsubstituted C$_1$–C$_6$ alkyl,
      d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, R$^{13}$O—, R$^{12}$S(O)$_m$—, R$^{11}$C(O)NR$^{11}$—, (R$^{11}$)$_2$NC(O)—, R$^{11}$$_2$N—C(NR$^{11}$)—, R$^{11}$C(O)—, —N(R$^{11}$)$_2$, and R$^{12}$OC(O)—NR$^{11}$—;

R$^6$ is selected from: hydrogen, halogen, trifluoromethyl, trifluoromethoxy and C$_1$–C$_6$ alkyl;
   R$^7$ is hydrogen;
   R$^8$, R$^9$ and R$^{10}$ are independently selected from:
      a) hydrogen,
      b) C$_3$–C$_{10}$ cycloalkyl, halogen, C$_1$–C$_6$ perfluoroalkyl, R$^{13}$O—, R$^{12}$S(O)$_m$—, R$^{11}$C(O)— or —N(R$^{11}$)$_2$,
      c) unsubstituted C$_1$–C$_6$ alkyl,
      d) substituted C$_1$–C$_6$ alkyl wherein the substituent on the substituted C$_1$–C$_6$ alkyl is selected from unsubstituted or substituted aryl, C$_3$–C$_{10}$ cycloalkyl, R$^{13}$O—, R$^{12}$S(O)$_m$—, R$^{11}$C(O)— or —N(R$^{11}$)$_2$;

A is:
   a 6 membered carbocyclic ring wherein from 0 to 2 carbon atoms are replaced by a heteroatom selected fom N, S and O, and wherein A is attached to B through a carbon atom;

B is:
   a 5 or 6 membered heterocyclic ring which comprises a nitrogen atom through which B is attached to A and 0–1 additional heteroatoms selected from N, S and O, and which also comprises a carbonyl or sulfonyl moiety adjacent to the nitrogen atom attached to A;

R$^{11}$ is independently selected from hydrogen, C$_1$–C$_6$ alkyl, benzyl, 2,2,2-trifluoroethyl, aryl and substituted aryl;

R$^{12}$ is independently selected from C$_1$–C$_6$ alkyl and aryl;

R$^{13}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted heteraryl, C$_1$–C$_6$ perfluoroalkyl, 2-aminoethyl and 2,2,2-trifluoroethyl;

m is 0, 1 or 2.

7. The process according to claim 1, wherein the compound of formula (I) is:

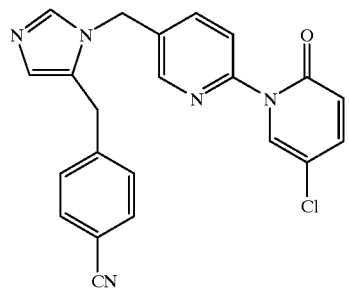

and the thioimidazole of the formula (II) is:

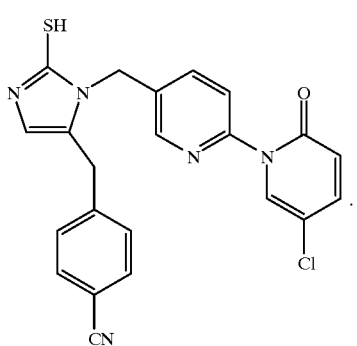

8. The process according to claim 1, wherein the thioimidazole of formula (II) is dethionated with aqueous $NaNO_2$ and HOAc.

9. The process according to claim 1, wherein the thioimidazole of formula (II) is prepared by condensing a hydroxyketone of the formula (III):

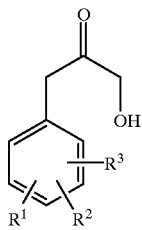

(III)

wherein $R^1$, $R^2$ and $R^3$ are defined as set forth in claim 1;

with a benzylic amine of the formula (IV):

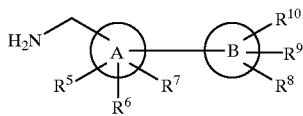

(IV)

wherein $R^5$, $R^6$, $R^7$, $R^8$, $R^9$, $R^{10}$, A and B are defined as set forth in claim 1;

in the presence of a thiocyanate and an acid.

10. The process according to claim 9, wherein the thiocyanate is selected from NaSCN and KSCN.

11. The process according to claim 10, wherein the thiocyanate is KSCN.

12. The process according to claim 9, wherein the acid is selected from: anhydrous or aqueous HF, HCl, HBr, HI, ammonium halides and carboxylic acids such as HOAc and TFA.

13. The process according to claim 12, wherein the acid is HOAc.

14. The process according to claim 9, wherein the hydroxy ketone of formula (III) is:

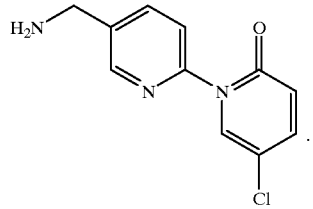

and the benzylic amine of formula (IV) is:

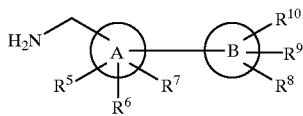

15. A compound of the formula (II):

(II)

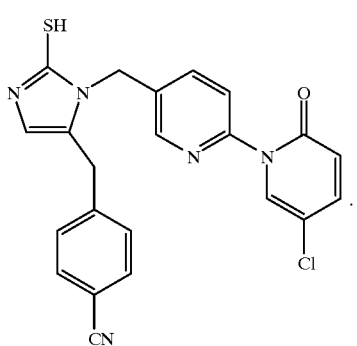

wherein:
  $R^1$, $R^2$ and $R^3$ are independently selected from:
    a) hydrogen,
    b) aryl, substituted aryl, heterocycle, substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{11}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{11}_2N$—C$(NR^{11})$—, CN, $NO_2$, $R^{11}C(O)$—, $N_3$, —$N(R^{11})_2$, or $R^{12}OC(O)NR^{11}$—, and
    c) $C_1$–$C_6$ alyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{11}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{11}_2N$—C$(NR^{11})$—, CN, $R^{11}C(O)$—, $N_3$, —$N(R^{11})_2$, or $R^{11}OC(O)NH$—;
  $R^5$, $R^6$ and $R^7$ are independently selected from:
    a) hydrogen,
    b) unsubstituted or substituted aryl, unsubstitued or substituted heterocycle, $C_3$–$C_{10}$ cycloalkyl, halogen, $C_1$–$C_6$ perfluoroalkyl, $R^{13}O$—, $R^{12}S(O)_m$—, $R^{11}C(O)NR^{11}$—, $(R^{11})_2NC(O)$—, $R^{12}C(O)O$—, $R^{11}_2N$—C$(NR^{11})$—, $R^{11}C(O)$—, —$N(R^{11})_2$, or $R^{12}OC(O)NR^{11}$—,
    c) unsubstituted $C_1$–$C_6$ alkyl,
    d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $R^{13}O$—, $R^{12}S(O)_m$—, $R^{11}C(O)NR^{11}$—, $(R^{11})_2NC(O)$—, $R^{11}{}_2N$—$C(NR^{11})$—, $R^{11}C(O)$—, —$N(R^{11})_2$, and $R^{12}OC(O)$—$NR^{11}$—;

$R^8$, $R^9$ and $R^{10}$ are independently selected from:
a) hydrogen,
b) unsubstituted or substituted aryl, unsubstituted or substituted heterocycle, $C_3$–$C_{10}$ cycloalkyl, halogen, $C_1$–$C_6$ perfluoroalkyl, $R^{13}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{12}C(O)O$—, $R^{11}{}_2N$—$C(NR^{11})$—, $R^{11}C(O)$—, —$N(R^{11})_2$, or $R^{12}OC(O)NR^{11}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $R^{13}O$—, $R^{12}S(O)_m$—, $R^{11}C(O)NR^{11}$—, $(R^{11})_2NC(O)$—, $R^{12}S(O)_2NR^{11}$—, $(R^{11})_2NS(O)_2$—, $R^{11}{}_2N$—$C(NR^{11})$—, $R^{11}C(O)$—, —$N(R^{11})_2$, and $R^{12}OC(O)$—$NR^{11}$—; or
any two of $R^8$, $R^9$ and $R^{10}$ on adjacent carbon atoms are combined to form a diradical selected from —CH=CH—CH=CH—, —CH=CH—CH$_2$—, —(CH$_2$)$_4$— and —(CH$_2$)$_3$—;

A is:
a 5, 6 or 7 membered carbocyclic ring wherein from 0 to 3 carbon atoms are replaced by a heteroatom selected from N, S and O, and wherein A is attached to B through a carbon atom;

B is:
a 4, 5, 6 or 7 membered heterocyclic ring which comprises a nitrogen atom through which B is attached to A and 0–2 additional heteroatoms selected from N, S and O, and which also comprises a carbonyl, thiocarbonyl, —C(=NR$^{14}$)— or sulfonyl moiety adjacent to the nitrogen atom attached to A;

$R^{11}$ is independently selected from hydrogen, $C_1$–$C_6$ alkyl, amino-$C_1$–$C_6$ alkyl, N-(unsubstituted or substituted benzoyl)-amino-$C_1$–$C_6$ alkyl, ($C_1$–$C_6$ alkyl)$_2$-amino-$C_1$–$C_6$ alkyl, acetylamino-$C_1$–$C_6$ alkyl, phenyl-$C_1$–$C_6$ alkyl, 2,2,2-trifluoroethyl, aryl and substituted aryl;

$R^{12}$ is independently selected from $C_1$–$C_6$ alkyl and aryl;

$R^{13}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$R^{14}$ is selected from hydrogen, $C_1$–$C_6$ alkyl, $C_1$–$C_6$ alkylsulfnyl and $C_1$–$C_6$ acyl;

m is 0, 1 or 2; and pharmaceutically acceptable salts thereof.

16. The compound according to claim 15 the formula:

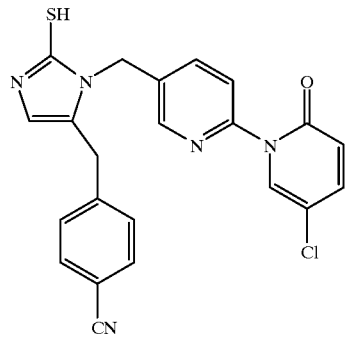

and pharmaceutically acceptable salts thereof.

* * * * *